United States Patent
Lacaze et al.

(10) Patent No.: US 11,596,144 B2
(45) Date of Patent: Mar. 7, 2023

(54) METHOD OF DETECTING AN INSECT INFESTATION

(71) Applicant: CENTRE SCIENTIFIQUE ET TECHNIQUE DU BATIMENT (CSTB), Champs sur Marne (FR)

(72) Inventors: Isabelle Lacaze, Chelles (FR); Stéphane Moularat, Torcy (FR); Enric Robine, Conches-sur-Gondoire (FR)

(73) Assignee: CENTRE SCIENTIFIQUE ET TECHNIQUE DU BATIMENT (CSTB), Champs sur Marne (FR)

( * ) Notice: Subject to any disclaimer, the term of this patent is extended or adjusted under 35 U.S.C. 154(b) by 185 days.

(21) Appl. No.: 16/954,757

(22) PCT Filed: Dec. 21, 2018

(86) PCT No.: PCT/FR2018/053509
§ 371 (c)(1),
(2) Date: Jun. 17, 2020

(87) PCT Pub. No.: WO2019/122781
PCT Pub. Date: Jun. 27, 2019

(65) Prior Publication Data
US 2020/0315158 A1    Oct. 8, 2020

(30) Foreign Application Priority Data
Dec. 21, 2017    (FR) ..................... 17 62893

(51) Int. Cl.
*A01M 31/00* (2006.01)
*G01N 33/00* (2006.01)
*A01M 1/00* (2006.01)

(52) U.S. Cl.
CPC ....... *A01M 31/002* (2013.01); *G01N 33/0047* (2013.01); *A01M 1/00* (2013.01); *A01M 2200/01* (2013.01)

(58) Field of Classification Search
CPC ............ G01N 2291/0257; A01M 1/00; A01M 31/002; A01M 2200/01
See application file for complete search history.

(56) References Cited

U.S. PATENT DOCUMENTS

| 6,255,652 B1 * | 7/2001 | Moyer ............... G01N 21/3504 250/343 |
| 2007/0157323 A1 * | 7/2007 | Carlson ................ C07K 14/72 435/348 |
| 2014/0080173 A1 * | 3/2014 | Moularat ................. C12Q 1/04 435/34 |
| 2017/0064942 A1 * | 3/2017 | Kelly .................. G01N 1/2202 |
| 2017/0233784 A1 | 8/2017 | Moularat et al. |

FOREIGN PATENT DOCUMENTS

| FR | 2913501 A1 | 9/2008 |
| JP | 2004-538286 A | 12/2004 |
| JP | 2017-536108 A | 12/2017 |

OTHER PUBLICATIONS

International Search Report dated May 20, 2019 in corresponding International Application No. PCT/FR2018/053509; 6 pages.
Sai Xu et al., "Recognition of the Duration and Prediction of Insect Prevalence of Stored Rough Rice Infested by the Red Flour Beetle (*Tribolium castaneum* Herbst) Using an Electronic Nose", Sensors, Apr. 14, 2017, vol. 17, No. 4, p. 688 1-9 to 9-9.
Brittany D. Lampson et al., "Development of a Portable Electronic Nose for Detection of Cotton Damaged by Nezara viridula (Hemiptera: Pentatomidae)", Journal of Insects, Nov. 11, 2014, vol. 2014, pp. 1-8.
J. Wu et al., "Feasibility of the application of electronic nose technology to detect insect infestation in wheat", Canadian Biosystems Engineering, Dec. 31, 2013, vol. 55, No. 1, pp. 3.1-3.9.

* cited by examiner

*Primary Examiner* — Christopher D Hutchens
(74) *Attorney, Agent, or Firm* — Maier & Maier, PLLC

(57) ABSTRACT

A method of detecting the presence of insects, including larvae, in an indoor environment, which includes the steps of (a) obtaining a sample of volatile organic compounds (VOCs); (b) separating the sampled VOCs; (c) detecting the presence or absence of "target" VOCs from at least one category: "category 1 VOCs"—VOCs emitted independently of the support on which the insects develop and emitted only in an insect infestation VOCs, "category 2 VOCs"—VOCs emitted independently of the support but may have biological origins other than insects, and "category 3 VOCs"—VOCs emitted depending on the support and emitted only in an insect infestation; (d) calculating both an insect infestation index ("3I") and a limit value ("VL") based on the presence or absence of the target VOCs; and (e) comparing the "3I" and "VL" values. The environment is infested for a "3I" value strictly greater than the "VL" value.

5 Claims, No Drawings

METHOD OF DETECTING AN INSECT INFESTATION

FIELD

The present invention relates to a method of detecting an insect infestation, including in the larval state in indoor environments.

BACKGROUND

"Indoor environment" means a enclosed or confined space inside a building that is ventilated discontinuously (via the openable windows, etc.) or continuously by forced ventilation. Examples of indoor environments may be found in dwellings, museums, churches, cellars, historic monuments, office buildings, schools and hospitals.

Insects are feared pests in many enclosed spaces. They notably attack frames, furniture, wooden panelling, fabrics, foodstuffs etc., and cause irreversible degradation leading to loss of mechanical strength of building components, destruction of heritage artifacts or loss of stored cereals.

The current techniques for detecting them are based essentially on detecting the adult insect, after degradation, and not in the larval state, though the latter is responsible for the damage. Thus, the conventional techniques do not allow a preventive strategy to be put in place, making it possible to treat the environments or at least establish active degradation.

In this context, early detection of these insect pests constitutes a major objective for preventing degradation of habitat, heritage artifacts or foodstuffs and thus limiting the use of curative treatments and the associated high costs of remediation, restoration, prevention etc.

One of the aims of the present invention is therefore early detection of the presence of insect pests, even in the larval state. "Early" detection means detection of the presence of insect pests before visible signs appear. Early detection is of great importance in heritage sites such as historic monuments, churches or museums, where irremediable damage has generally already been caused when the first visible signs of an infestation appear.

In application FR 2 913 501 titled "Method of detecting fungal contamination" the applicant determined a "chemical index of fungal contamination", called "ICF", which makes it possible to detect fungal contamination in an indoor environment.

However, the method for calculating the ICF described in said document FR 2 913 501 does not make it possible to be sufficiently specific concerning the detection of insects. Consequently it is not transferable as it is, and needs to be improved.

The applicant therefore continued to conduct research, undertaking work based on detecting larvae from the volatile organic compounds (VOCs) resulting from their metabolism and/or degradation of the substrates. These target VOCs are dispersed in the environment and are not retained by the substrates. More particularly, the applicant has now found that certain VOCs are only present in the ambient air in the presence of insects, including in the larval state. These VOCs therefore specifically result from the insects' metabolism, including in the larval state. It was also found that certain other VOCs are present in the ambient air not only in the presence of the insects, but also in the presence of certain materials or other biological contaminations.

SUMMARY

Based on this discovery, the applicant has been able to demonstrate that these VOCs specific to insects can be divided into two groups:
  VOCs that are emitted independently of the substrate on which the insects grow, and
  VOCs that are emitted as a function of the substrate on which the insects grow.

Among the VOCs that are emitted independently of the substrate, a distinction is made between the VOCs that are only emitted by insects and the VOCs that may have biological origins other than insects.

Thus, three separate categories of VOCs were determined. The invention is based on determination and detection of these VOCs specific to insects, also called predetermined "target" VOCs.

In fact, detection of these predetermined target VOCs on the one hand allows early detection of an infestation and on the other hand detection of infestations that are not visible to the naked eye.

The applicant has more particularly developed an "Insect Infestation Index" value represented by "3I"" (also called 3I index) and a value called "Limit Value" represented by "VL", each of which is dependent on the presence or absence of the predetermined target VOCs. By determining and comparing these values, early detection of the presence of insects, even in the larval state, becomes possible.

Therefore, after extensive, long-term research, the applicant was able to elaborate a method of detecting an insect infestation, including in the larval state, in indoor environments even in the absence of visible signs of infestation.

DETAILED DESCRIPTION

The present invention relates more particularly to a method of detecting the presence of insects in an indoor environment comprising:
  a/ taking a sample of volatile organic compounds (VOCs) in the indoor environment;
  b/ separating the VOCs sampled;
  c/ detecting the presence or absence of predetermined "target" VOCs, these predetermined "target" VOCs belonging to at least one of the following three categories of VOCs:
  VOCs that are emitted independently of the substrate on which the insects grow, and that are only emitted during an insect infestation, called "category 1 VOCs";
  VOCs that are emitted independently of the substrate on which the insects grow but that may also have biological origins other than insects, called "category 2 VOCs";
  VOCs that are emitted as a function of the substrate on which the insects grow, and that are only emitted during an insect infestation, called "category 3 VOCs";
  d/ calculating respectively a value "Insect Infestation Index" called "3I" (or "3I index") and a value "Limit Value" called "VL", each of which depends on the presence or absence of the predetermined target VOCs,
  e/ comparing the values "3I" and "VL"; if the value "3I" is strictly greater than the value "VL", the environment is infested, and if the value "3I" is less than or equal to the value "VL" then the environment is not infested.

According to the method of the invention, step a/ of taking the sample of VOCs is preferably carried out by active or diffusive sampling on a solid adsorbent preferably selected from activated carbon, silica gel, zeolites and porous synthetic resins, such as those marketed under the trademarks Tenax®, Carbograph® or Chromosorb®.

In this case, the method of the invention also comprises a step of desorption of the adsorbed VOCs. The latter is carried out by thermo-desorption in conditions that are familiar to a person skilled in the art.

The method of the invention also comprises separation of the sampled VOCs (step b/). In particular, the sampled VOCs are separated by elution on a chromatographic microcolumn. The optimal separation parameters, such as column temperature or flow rate of the mobile phase, are determined by techniques familiar to a person skilled in the art as a function of column geometry, and the nature of the stationary phase and of the carrier gas.

The detection step c/ makes it possible to detect the presence or absence of predetermined "target" VOCs, resulting from the insects' metabolism, including in the larval state. These predetermined "target" VOCs, in conjunction with the activity of the insects, including in the larval state, comprise at least one VOC of one of the categories 1, 2 or 3.

Detecting the presence or absence of at least one predetermined target VOC of each of the three categories of VOCs stated above increases the certainty of the method of detection according to the invention relative to detection of the presence or absence of VOCs from just one of these categories.

Preferably, several target VOCs of each of the three aforementioned categories will be detected.

The predetermined target VOCs are for example detected by gas chromatography followed by mass spectrometry (GC/MS).

The next step d/ of the method of the invention then consists of calculating the value "Insect Infestation Index" ("3I" or 3I index) and the value "Limit Value" ("VL").

More particularly, according to the invention, step d/ is carried out in three substeps:

d-1/ determining an incrementing value "i", the incrementing value being obtained by assigning, to each of the predetermined target VOCs, a number −1, 0 or 1 depending on its presence or its absence, the numbers being assigned as follows:
presence of a VOC of category (1) is characterized by the number 1 and its absence by −1;
presence of a VOC of category (2) is characterized by the number 0 and its absence by −1;
presence of a VOC of category (3) is characterized by the number 1 and its absence by 0;

d-2/ determining a weighting value "P" (also called "weighting factor") corresponding to the following formula:

$$P = \frac{\text{Coefficient 1}}{\text{Number of "weighted } VOCs\text{"}}$$

in which:
the "weighted VOCs" correspond to the VOCs found on substrates without active infestation but emitted in a larger relative amount in the presence of the insects, namely in an amount at least two times higher,
coefficient 1 is an empirical real number established by iteration with a panel of environments whose infestation is known;

d-3/ determining the value 3I and VL,
the value (3I) corresponding to the following formula:

$$(3I) = \Sigma_{j=1}^{n} i_j \times P_j$$

in which:
n represents the number of target VOCs,
j represents an integer,
i represents the incrementing value as defined in step d-1/,
P represents the weighting value as defined in step d-2/,
$i_j$ represents the incrementation of the j-th target VOC,
$P_j$ represents the weighting of the j-th target VOC,
the value (VL) corresponding to the following formula:

$$VL = \frac{\text{Number of "unweighted } VOCs\text{"} + P \times \text{Number of "weighted } VOCs\text{"}}{\text{Coefficient 2}}$$

in which the "unweighted VOCs" correspond to the VOCs only emitted in the presence of insects,
the coefficient 2 is an empirical real number established by iteration with the same environment panel as that used for determining "coefficient 1".

Coefficient 1 is therefore fixed for allowing discrimination of the two groups of the panel (infested/uninfested). This coefficient is a function of the insect species to be detected.

Similarly, coefficient 2 is fixed for allowing discrimination of the two groups of the panel (infested/uninfested). This coefficient is a function of the insect species to be detected.

Firstly (step d-1/) it is a matter of determining an incrementing value "i", which is a function of the presence or absence of each predetermined target VOC.

More particularly, during the research, the applicant made the following findings.

The presence of VOCs specifically resulting from insects' metabolism, including in the larval state, which are emitted independently of the substrate on which the insects grow, and are only emitted during an insect infestation (category 1 VOCs), indicates an insect infestation, whereas the absence of such VOCs indicates absence of an insect infestation.

In contrast, the presence of VOCs specifically resulting from insects' metabolism, including in the larval state, which are emitted independently of the substrate on which the insects grow and which may also have biological origins other than insects (category 2 VOCs) does not allow a conclusion of insect infestation. However, absence of such VOCs indicates absence of an insect infestation.

Regarding the VOCs specifically resulting from insects' metabolism, including in the larval state, that are emitted as a function of the substrate on which the insects grow, and that are only emitted during an insect infestation (category 3 VOCs), their presence indicates an insect infestation, whereas their absence does not allow a conclusion of absence of an insect infestation.

Based on these findings, a method of calculation was elaborated by the inventors, which is based on the following incrementation.

The presence of a VOC is incremented by a value "1" if the presence of the VOC indicates an insect infestation and by a value "0" if the presence of the VOC does not allow a conclusion of the presence of an insect infestation. The absence of a VOC is incremented by a value "−1" if absence of the VOC indicates absence of an insect infestation and by a value "0" if absence of the VOC does not allow a conclusion of absence of insect infestation.

Table 1 below summarizes the principles of incrementation.

TABLE 1

| | Incrementation "i" | |
|---|---|---|
| VOCs | presence | absence |
| emitted independently of the substrate, only emitted during an insect infestation (category 1) | 1 | −1 |
| emitted independently of the substrate, may also have other biological origins (category 2) | 0 | −1 |
| emitted as a function of the substrate, only emitted during an insect infestation (category 3) | 1 | 0 |

However, this first step d-1/ does not by itself make it possible to discriminate infested environments from "healthy" environments.

Consequently, in order to allow this discrimination, a second step d-2/, which consists of weighting, makes it possible to complete this first step.

The VOCs found in the laboratory in the context of reference (substrate without active infestation), but emitted in a larger relative amount in the presence of the insects (amount at least 2 times higher), are taken into account here and weighted by a factor called "P", defined as follows:

$$P = \frac{\text{Coefficient 1}}{\text{Number of "weighted } VOCs\text{"}}$$

These VOCs are called "weighted VOCs". This weighting has the aim of reducing the effect of these compounds ("weighted VOCs") with respect to compounds emitted only by insects ("unweighted VOCs") in the laboratory.

Thus, detection of n "weighted VOCs" (n=Number of "weighted VOCs"=Coefficient 1/P), is equivalent to 1 "unweighted VOC".

"Coefficient 1" is an empirical real number determined experimentally with measurements in situ. This coefficient was established by iteration with a panel of environments whose infestation is known (infested/uninfested).

This weighting P is equal to 1 (P=1) in the case of the VOCs only emitted in the presence of insects "unweighted VOCs". This unit weighting makes it possible to give the same importance to each "unweighted VOC".

Finally, the third step d-3/ makes it possible to determine the values "3I" (3I index) and "VL", respectively.

The 3I index is incremented as follows:

$$(3I) = \Sum_{j=1}^{n} i_j \times P_j$$

with n, j, i, P, $P_j$ as defined above, namely:
n represents the number of target VOCs,
j represents an integer,
i represents the incrementing value as defined in step e1/,
P represents the weighting value as defined in step e2/,
$i_j$ represents the incrementation of the j-th target VOC,
$P_j$ represents the weighting of the j-th target VOC,
The value (VL) corresponds to the formula already described, namely:

$$VL = \frac{\text{Number of "unweighted } VOCs\text{" + } P \times \text{Number of "weighted } VOCs\text{"}}{\text{Coefficient 2}}$$

"Coefficient 2" is an empirical real number determined experimentally with the measurements in situ. As before for "coefficient 1", "coefficient 2" was established by iteration with the same environment panel as was used for determining "coefficient 1".

These coefficients "1" and "2" make it possible, by an empirical approach, to discriminate two separate groups (infested and uninfested) from a panel of environments whose state of infestation is known.

If index (3I) is strictly greater than VL (3I>VL), then the environment is infested, but if on the contrary index (3I) is less than or equal to VL (3I≤VL) it is not infested.

According to the invention, the predetermined target VOCs are preferably selected from the group comprising 2,2'-bi-1,3-dioxolane; n-butyl acetate; 1,3,5,7-cyclooctatetraene; alpha-pinene; 1-propanol; methanecarbothiolic acid; 3,3-dimethyl-1-hexene; 2-butanone; ethyl acetate; 4-hydroxy-2-butanone; 1-butanol; 2,5-dimethyl-furan; 2-ethenyl-2-butenal; butyl formate; pyrazine; pyrrole; 1-pentanol; 1-(3,4-dimethylthieno[2,3-b]thiophen-2-yl)-ethanone-oxime; 1,4-octadiene; 1,3-octadiene; 2-methyl-pyrimidine; 1-hexanol; 2-heptanone; 2,5-dimethyl-pyrazine; camphene; 2-octanone; 1-methyl-4-(1-methylethenyl)-cyclohexene; 2-methyldecane; acetophenone; 2-nonen-1-ol; 1,10-dichlorodecane; dodecanal; 2-pentyl-thiophene; 2-decen-1-ol; naphthalene; diethyl phthalate, and mixtures thereof.

More particularly, according to an advantageous embodiment of the invention:
the predetermined target category 1 VOCs are selected from the group comprising 2,2'-bi-1,3-dioxolane and n-butyl acetate;
the predetermined target category 2 VOCs are selected from the group comprising 1,3,5,7-cyclooctatetraene and alpha-pinene;
the predetermined target category 3 VOCs are selected from the group comprising 1-propanol; methanecarbothiolic acid; 3,3-dimethyl-1-hexene; 2-butanone; ethyl acetate; 4-hydroxy-2-butanone; 1-butanol; 2,5-dimethyl-furan; 2-ethenyl-2-butenal; butyl formate; pyrazine; pyrrole; 1-pentanol; 1-(3,4-dimethylthieno[2,3-b]thiophen-2-yl)-ethanone-oxime; 1,4-octadiene; 1,3-octadiene; 2-methyl-pyrimidine; 1-hexanol; 2-heptanone; 2,5-dimethyl-pyrazine; camphene; 2-octanone; 1-methyl-4-(1-methylethenyl)-cyclohexene; 2-methyldecane; acetophenone; 2-nonen-1-ol; 1,10-dichlorodecane; dodecanal; 2-pentyl-thiophene; 2-decen-1-ol; naphthalene and diethyl phthalate.

The method of detecting an insect infestation according to the invention is particularly useful for early detection of such an infestation, i.e. before visible signs appear.

The invention also relates to a method of detecting the presence of insects as defined above, characterized in that the insects are in the larval state.

The following embodiment example illustrates the present invention, without limiting its scope in any way.

EXAMPLE

The aim of the work presented below is to determine, in a first laboratory phase, a list of target VOCs emitted during infestation of substrates by an insect at the larval stage. In practice, infested and uninfested substrates will be placed in emission chambers before taking samples of the VOCs.

In the second phase, the targets VOCs will be sought in samples taken from indoor environments that do or do not have an infestation by these insects.

Material and Methods
Biological Material

The insect species used is a keratophagous microlepidopteron, the clothes moth, *Tineola bisselliella*. In the laboratory phase, two or three larvae of this species obtained from a breeding station were deposited in the chambers, which were called "infested chambers".

According to one embodiment of the detection method of the invention, when the insect is *Tineola bisselliella*, then:
- coefficient 1 has a value from 1 to 3, and is preferably equal to 2,
- coefficient 2 has a value from 3 to 5, and is preferably equal to 4.

Growth Substrate

Two types of substrates, vulnerable to moths, are used in the laboratory phase:
- a piece of woven wool,
- rabbit skin.

Emission Chamber

Emission chambers of 300 $cm^3$, developed by CSTB, are used in the laboratory phase. They are made of glass and are equipped with PTFE valves for taking the VOC samples.

For each series of analyses, a reference chamber, free from moths and containing only the nutrient substrate, namely wool or rabbit skin, was used. The emission chambers are then incubated in an incubator at a temperature of 25° C., away from the light. The incubation time varies depending on the experiments conducted, and is between 3 and 6 months.

Environments In Situ

Three types of environment were investigated. Visual diagnosis and diagnosis coupled with the use of pheromone traps were carried out for determining the presence or absence of clothes moths in the different places examined. These are a palace located in the Ile-de-France region (2 rooms), two dwellings and a museum (in an infested horse-drawn carriage and in the shed).

Table 2 describes the environments investigated and their state of infestation.

TABLE 2

Environments investigated and state of infestation

| Type | Place | State of infestation |
|---|---|---|
| Palace | Palace 1 | Infested |
|  | Palace 2 | Infested |
| Museum | Carriage int | Infested |
|  | Carriage ext | Not infested |
| Dwelling | Dwelling 1 | Not infested |
|  | Dwelling 2 | Not infested |

Sampling

The VOCs are collected in tubes containing an adsorbent, TENAX® TA (Sigma Aldrich). This is an apolar phase, consisting of an adsorbent polymer of 2,6-diphenyl-p-phenylene oxide. The latter makes it possible to retain the molecules whose number of carbons is between $C_4$ and $C_{20}$. Sampling is active, and is carried out using a pump. The sampling flow rate is fixed at 100 $cm^3$/min and the sampling time is sufficient for renewing the chamber volume at least ten times.

In the case of environmental sampling carried out in enclosed spaces, the flow rate is 150 $cm^3$/min and the sampling time is one hour.

Analysis

Desorption of the tubes of TENAX® TA is carried out on an ATD 400, Perkin Elmer. The VOCs are injected simultaneously on a column of the VF-5 ms type (Agilent); they are then separated and analyzed with a GC-MS system (GC 3800-MS Saturn 2000, Varian). The analytes are identified from their retention and by comparing their mass spectrum with the NIST 2008 library. Identification of the compounds is confirmed by passage of a standard, depending on availability.

Results
Laboratory Phase

This phase makes it possible to identify a list of target VOCs emitted during insect infestation of substrates. Each target VOC was then assigned to one of the three categories "category 1, 2 or 3" as described in the present application (classification of the VOCs produced according to their specificity).

The presence or absence of the target VOC ("category 1, 2 or 3") in the reference context made it possible to determine an incrementation "i" and then the weighting P, and finally the 3I index.

In the present case, the following are obtained, respectively:
- a weighting P equal to 1 for the "unweighted VOCs",
- a weighting P equal to 0.08 for the "weighted VOCs".

The weighting P less than 1 (P=0.08) makes it possible to limit the effect of a "weighted VOC". Thus, several weighted VOCs are necessary to have the same effect as an "unweighted VOC".

The results obtained are presented in Table 3.

Regarding the column "Presence/Absence", the number 0 indicates absence of the VOCs and the number 1 indicates presence of the VOCs.

Regarding the column "Incrementation", the numbers 1, 0 and −1 are as described in Table 1.

TABLE 3

Emission of the VOCs on uninfested, previously infested and infested substrates

| | Presence/Absence | | | | | | | | |
|---|---|---|---|---|---|---|---|---|---|
| | Uninfested wool (reference 1) | Uninfested wool (reference 2) | Uninfested rabbit skin (reference) | Previously infested wool 1 | Previously infested wool 2 | Infested wool 1 | Infested wool 2 | Infested wool 3 | Infested wool 4 |
| 1-propanol | 0 | 0 | 1 | 0 | 0 | 0 | 1 | 1 | 0 |
| Methanecarbothiolic acid | 0 | 1 | 0 | 0 | 1 | 1 | 0 | 1 | 1 |
| 3,3-dimethyl-1-Hexene | 0 | 0 | 0 | 0 | 0 | 1 | 0 | 0 | 0 |
| 2-Butanone | 0 | 0 | 1 | 0 | 0 | 0 | 0 | 0 | 1 |
| Ethyl Acetate | 0 | 0 | 0 | 0 | 1 | 0 | 1 | 0 | 1 |
| 4-hydroxy-2-Butanone | 0 | 0 | 1 | 0 | 0 | 0 | 0 | 0 | 0 |

TABLE 3-continued

Emission of the VOCs on uninfested, previously infested and infested substrates

| | | | | | | | | | |
|---|---|---|---|---|---|---|---|---|---|
| 2,2'-Bi-1,3-dioxolane | 1 | 0 | 0 | 0 | 0 | 1 | 1 | 1 | 1 |
| 1-Butanol | 0 | 1 | 1 | 0 | 1 | 0 | 1 | 1 | 1 |
| 2,5-dimethyl-Furan | 0 | 1 | 0 | 0 | 1 | 0 | 1 | 1 | 1 |
| 2-ethenyl-2-Butenal | 0 | 0 | 1 | 0 | 1 | 0 | 0 | 1 | 1 |
| Butyl formate | 0 | 1 | 0 | 0 | 0 | 0 | 1 | 0 | 1 |
| Pyrazine | 0 | 0 | 0 | 0 | 0 | 0 | 0 | 1 | 0 |
| Pyrrole | 0 | 0 | 0 | 0 | 0 | 0 | 1 | 0 | 0 |
| 1-Pentanol | 0 | 0 | 1 | 1 | 1 | 0 | 0 | 0 | 1 |
| 1-(3,4-dimethylthieno[2,3-b]thiophen-2-yl)-Ethanoneoxime | 0 | 0 | 0 | 0 | 0 | 1 | 0 | 0 | 0 |
| n-Butyl acetate | 0 | 0 | 1 | 0 | 1 | 0 | 1 | 0 | 1 |
| 1,4-Octadiene | 0 | 0 | 0 | 0 | 0 | 0 | 1 | 0 | 1 |
| 1,3-Octadiene | 0 | 0 | 1 | 0 | 0 | 0 | 0 | 0 | 0 |
| 2-methyl-Pyrimidine | 0 | 0 | 0 | 0 | 0 | 0 | 0 | 1 | 0 |
| 1-Hexanol | 0 | 0 | 1 | 0 | 0 | 0 | 0 | 1 | 1 |
| 2-Heptanone | 1 | 0 | 1 | 0 | 1 | 0 | 0 | 0 | 1 |
| 1,3,5,7-Cyclooctatetraene | 1 | 1 | 1 | 1 | 1 | 1 | 1 | 0 | 1 |
| 2,5-dimethyl-Pyrazine | 0 | 0 | 0 | 0 | 0 | 1 | 0 | 0 | 0 |
| a-pinene | 0 | 1 | 1 | 1 | 1 | 1 | 1 | 1 | 1 |
| Camphene | 0 | 0 | 0 | 0 | 1 | 0 | 1 | 0 | 1 |
| 2-Octanone | 1 | 0 | 1 | 0 | 0 | 0 | 1 | 1 | 1 |
| 1-methyl-4-(1-methylethenyl)-Cyclohexene | 1 | 1 | 1 | 0 | 0 | 0 | 1 | 1 | 1 |
| 2-methyl-Decane | 0 | 0 | 0 | 0 | 0 | 0 | 0 | 0 | 0 |
| Acetophenone | 1 | 1 | 1 | 1 | 1 | 1 | 0 | 0 | 0 |
| 2-Nonen-1-ol | 1 | 1 | 1 | 1 | 1 | 1 | 1 | 1 | 1 |
| 1,10-Dichlorodecane | 1 | 0 | 0 | 0 | 1 | 0 | 1 | 1 | 1 |
| Dodecanal | 0 | 0 | 0 | 0 | 0 | 0 | 1 | 0 | 1 |
| 2-pentyl-Thiophene | 0 | 0 | 0 | 0 | 0 | 0 | 0 | 0 | 0 |
| 2-Decen-1-ol | 0 | 1 | 1 | 1 | 1 | 0 | 1 | 1 | 0 |
| Naphthalene | 1 | 1 | 1 | 1 | 1 | 1 | 1 | 1 | 1 |
| Diethyl Phthalate | 0 | 1 | 1 | 0 | 1 | 0 | 1 | 1 | 1 |

Index 3I

| | Presence/Absence | Incrementation (i) | | | | | |
|---|---|---|---|---|---|---|---|
| | Infested rabbit skin | VOC category | Incrementation if presence | Incrementation if absence | Weighting (P) | i × P if presence | i × P if absence | Wool (reference 1) |
| 1-propanol | 1 | 3 | 1 | 0 | 0.08 | 0.08 | 0 | 0 |
| Methanecarbothiolic acid | 0 | 3 | 1 | 0 | 0.08 | 0.08 | 0 | 0 |
| 3,3-dimethyl-1-Hexene | 0 | 3 | 1 | 0 | 0.08 | 0.08 | 0 | 0 |
| 2-Butanone | 1 | 3 | 1 | 0 | 0.08 | 0.08 | 0 | 0 |
| Ethyl Acetate | 0 | 3 | 1 | 0 | 1 | 1 | 0 | 0 |
| 4-hydroxy-2-Butanone | 1 | 3 | 1 | 0 | 0.08 | 0.08 | 0 | 0 |
| 2,2'-Bi-1,3-dioxolane | 1 | 1 | 1 | −1 | 1 | 1 | −1 | 1 |
| 1-Butanol | 1 | 3 | 1 | 0 | 0.08 | 0.08 | 0 | 0 |
| 2,5-dimethyl-Furan | 1 | 3 | 1 | 0 | 0.08 | 0.08 | 0 | 0 |
| 2-ethenyl-2-Butenal | 1 | 3 | 1 | 0 | 0.08 | 0.08 | 0 | 0 |
| Butyl formate | 0 | 3 | 1 | 0 | 0.08 | 0.08 | 0 | 0 |
| Pyrazine | 1 | 3 | 1 | 0 | 1 | 1 | 0 | 0 |
| Pyrrole | 1 | 3 | 1 | 0 | 1 | 1 | 0 | 0 |
| 1-Pentanol | 1 | 3 | 1 | 0 | 0.08 | 0.08 | 0 | 0 |
| 1-(3,4-dimethylthieno[2,3-b]thiophen-2-yl)-Ethanoneoxime | 0 | 3 | 1 | 0 | 1 | 1 | 0 | 0 |
| n-Butyl acetate | 1 | 1 | 1 | −1 | 0.08 | 0.08 | −0.08 | −0.08 |
| 1,4-Octadiene | 0 | 3 | 1 | 0 | 1 | 1 | 0 | 0 |
| 1,3-Octadiene | 1 | 3 | 1 | 0 | 0.08 | 0.08 | 0 | 0 |
| 2-methyl-Pyrimidine | 1 | 3 | 1 | 0 | 1 | 1 | 0 | 0 |
| 1-Hexanol | 1 | 3 | 1 | 0 | 0.08 | 0.08 | 0 | 0 |
| 2-Heptanone | 1 | 3 | 1 | 0 | 0.08 | 0.08 | 0 | 0.08 |
| 1,3,5,7-Cyclooctatetraene | 1 | 2 | 0 | −1 | 0.08 | 0 | −0.08 | 0 |
| 2,5-dimethyl-Pyrazine | 1 | 3 | 1 | 0 | 1 | 1 | 0 | 0 |

TABLE 3-continued

Emission of the VOCs on uninfested, previously infested and infested substrates

| | | | | | | | | |
|---|---|---|---|---|---|---|---|---|
| a-pinene | 1 | 2 | 0 | −1 | 0.08 | 0 | −0.08 | −0.08 |
| Camphene | 0 | 3 | 1 | 0 | 1 | 1 | 0 | 0 |
| 2-Octanone | 1 | 3 | 1 | 0 | 0.08 | 0.08 | 0 | 0.08 |
| 1-methyl-4-(1-methylethenyl)-Cyclohexene | 1 | 3 | 1 | 0 | 0.08 | 0.08 | 0 | 0.08 |
| 2-methyl-Decane | 1 | 3 | 1 | 0 | 1 | 1 | 0 | 0 |
| Acetophenone | 1 | 3 | 1 | 0 | 0.08 | 0.08 | 0 | 0.08 |
| 2-Nonen-1-ol | 1 | 3 | 1 | 0 | 1 | 1 | 0 | 1 |
| 1,10-Dichlorodecane | 0 | 3 | 1 | 0 | 0.08 | 0.08 | 0 | 0.08 |
| Dodecanal | 0 | 3 | 1 | 0 | 1 | 1 | 0 | 0 |
| 2-pentyl-Thiophene | 1 | 3 | 1 | 0 | 1 | 1 | 0 | 0 |
| 2-Decen-1-ol | 0 | 3 | 1 | 0 | 0.08 | 0.08 | 0 | 0 |
| Naphthalene | 1 | 3 | 1 | 0 | 0.08 | 0.08 | 0 | 0.08 |
| Diethyl Phthalate | 1 | 3 | 1 | 0 | 0.08 | 0.08 | 0 | 0 |
| Index 3I | | | | | | | | 2.32 |

| | Incrementation (i) | | | | | | | |
|---|---|---|---|---|---|---|---|---|
| | Wool (reference 2) | Rabbit skin (reference) | Previously infested wool 1 | Previously infested wool 2 | Infested wool 1 | Infested wool 2 | Infested wool 3 | Infested wool 4 | Infested rabbit skin |
| 1-propanol | 0 | 0.08 | 0 | 0 | 0 | 0.08 | 0.08 | 0 | 0.08 |
| Methanecarbothiolic acid | 0.08 | 0 | 0 | 0.08 | 0.08 | 0 | 0.08 | 0.08 | 0 |
| 3,3-dimethyl-1-Hexene | 0 | 0 | 0 | 0 | 0.08 | 0 | 0 | 0 | 0 |
| 2-Butanone | 0 | 0.08 | 0 | 0 | 0 | 0 | 0 | 0.08 | 0.08 |
| Ethyl Acetate | 0 | 0 | 0 | 1 | 0 | 1 | 0 | 1 | 0 |
| 4-hydroxy-2-Butanone | 0 | 0.08 | 0 | 0 | 0 | 0 | 0 | 0 | 0.08 |
| 2,2'-Bi-1,3-dioxolane | −1 | −1 | −1 | −1 | 1 | 1 | 1 | 1 | 1 |
| 1-Butanol | 0.08 | 0.08 | 0 | 0.08 | 0 | 0.08 | 0.08 | 0.08 | 0.08 |
| 2,5-dimethyl-Furan | 0.08 | 0 | 0 | 0.08 | 0 | 0.08 | 0.08 | 0.08 | 0.08 |
| 2-ethenyl-2-Butenal | 0 | 0.08 | 0 | 0.08 | 0 | 0 | 0.08 | 0.08 | 0.08 |
| Butyl formate | 0.08 | 0 | 0 | 0 | 0 | 0.08 | 0 | 0.08 | 0 |
| Pyrazine | 0 | 0 | 0 | 0 | 0 | 0 | 1 | 0 | 1 |
| Pyrrole | 0 | 0 | 0 | 0 | 0 | 1 | 0 | 0 | 1 |
| 1-Pentanol | 0 | 0.08 | 0.08 | 0.08 | 0 | 0 | 0 | 0.08 | 0.08 |
| 1-(3,4-dimethylthieno[2,3-b]thiophen-2-yl)-Ethanoneoxime | 0 | 0 | 0 | 0 | 1 | 0 | 0 | 0 | 0 |
| n-Butyl acetate | −0.08 | 0.08 | −0.08 | 0.08 | −0.08 | 0.08 | −0.08 | 0.08 | 0.08 |
| 1,4-Octadiene | 0 | 0 | 0 | 0 | 0 | 1 | 0 | 1 | 0 |
| 1,3-Octadiene | 0 | 0.08 | 0 | 0 | 0 | 0 | 0 | 0 | 0.08 |
| 2-methyl-Pyrimidine | 0 | 0 | 0 | 0 | 0 | 0 | 1 | 0 | 1 |
| 1-Hexanol | 0 | 0.08 | 0 | 0 | 0 | 0 | 0.08 | 0.08 | 0.08 |
| 2-Heptanone | 0 | 0.08 | 0 | 0.08 | 0 | 0 | 0 | 0.08 | 0.08 |
| 1,3,5,7-Cyclooctatetraene | 0 | 0 | 0 | 0 | 0 | 0 | −0.08 | 0 | 0 |
| 2,5-dimethyl-Pyrazine | 0 | 0 | 0 | 0 | 1 | 0 | 0 | 0 | 1 |
| a-pinene | 0 | 0 | 0 | 0 | 0 | 0 | 0 | 0 | 0 |
| Camphene | 0 | 0 | 0 | 1 | 0 | 1 | 0 | 1 | 0 |
| 2-Octanone | 0 | 0.08 | 0 | 0 | 0 | 0.08 | 0.08 | 0.08 | 0.08 |
| 1-methyl-4-(1-methylethenyl)-Cyclohexene | 0.08 | 0.08 | 0 | 0 | 0 | 0.08 | 0.08 | 0.08 | 0.08 |
| 2-methyl-Decane | 0 | 0 | 0 | 0 | 0 | 0 | 0 | 0 | 1 |
| Acetophenone | 0.08 | 0.08 | 0.08 | 0.08 | 0.08 | 0 | 0 | 0 | 0.08 |
| 2-Nonen-1-ol | 1 | 1 | 1 | 1 | 1 | 1 | 1 | 1 | 1 |
| 1,10-Dichlorodecane | 0 | 0 | 0 | 0.08 | 0 | 0.08 | 0.08 | 0.08 | 0 |
| Dodecanal | 0 | 0 | 0 | 0 | 0 | 1 | 0 | 1 | 0 |
| 2-pentyl-Thiophene | 0 | 0 | 0 | 0 | 0 | 0 | 0 | 0 | 1 |
| 2-Decen-1-ol | 0.08 | 0.08 | 0.08 | 0.08 | 0 | 0.08 | 0.08 | 0 | 0 |
| Naphthalene | 0.08 | 0.08 | 0.08 | 0.08 | 0.08 | 0.08 | 0.08 | 0.08 | 0.08 |
| Diethyl Phthalate | 0.08 | 0.08 | 0 | 0.08 | 0 | 0.08 | 0.08 | 0.08 | 0.08 |
| Index 3I | 0.64 | 1.28 | 0.24 | 2.96 | 4.24 | 7.88 | 4.8 | 7.2 | 9.28 |

As already stated, for the value (3I) dedicated to *Tineola bisselliella*, the coefficients 1 and 2 are fixed at 2 and 4, respectively.

In Situ Phase

This phase makes it possible on the one hand to compare the list of target VOCs identified in the laboratory phase with several background noises encountered in real environments. On the other hand, it makes it possible to compare the emissions in infested and uninfested environments.

The results are presented in Table 4.

TABLE 4

Emission of VOCs from infested and uninfested environments

| | Presence/Absence | | | | | | Incrementation (i) | | |
|---|---|---|---|---|---|---|---|---|---|
| | Carriage ext | Dwelling 1 | Dwelling 2 | Carriage int | Palace 1 | Palace 2 | VOC category | Incrementation if presence | Incrementation if absence |
| 1-propanol | 1 | 0 | 0 | 0 | 1 | 1 | 3 | 1 | 0 |
| Methanecarbothiolic acid | 0 | 1 | 1 | 1 | 1 | 1 | 3 | 1 | 0 |
| 3,3-dimethyl-1-Hexene | 0 | 0 | 0 | 0 | 0 | 0 | 3 | 1 | 0 |
| 2-Butanone | 1 | 1 | 0 | 1 | 1 | 1 | 3 | 1 | 0 |
| Ethyl Acetate | 1 | 0 | 0 | 0 | 1 | 1 | 3 | 1 | 0 |
| 4-hydroxy-2-Butanone | 1 | 0 | 0 | 1 | 0 | 0 | 3 | 1 | 0 |
| 2,2'-Bi-1,3-dioxolane | 1 | 0 | 0 | 1 | 1 | 1 | 1 | 1 | −1 |
| 1-Butanol | 1 | 0 | 1 | 0 | 0 | 1 | 3 | 1 | 0 |
| 2,5-dimethyl-Furan | 0 | 0 | 0 | 0 | 0 | 0 | 3 | 1 | 0 |
| 2-ethenyl-2-Butenal | 0 | 0 | 0 | 0 | 0 | 0 | 3 | 1 | 0 |
| Butyl formate | 0 | 0 | 0 | 0 | 0 | 0 | 3 | 1 | 0 |
| Pyrazine | 0 | 1 | 1 | 0 | 0 | 0 | 3 | 1 | 0 |
| Pyrrole | 0 | 0 | 1 | 0 | 1 | 0 | 3 | 1 | 0 |
| 1-Pentanol | 1 | 0 | 0 | 1 | 1 | 1 | 3 | 1 | 0 |
| 1-(3,4-dimethylthieno[2,3-b]thiophen-2-yl)-Ethanoneoxime | 0 | 0 | 0 | 1 | 0 | 1 | 3 | 1 | 0 |
| n-Butyl acetate | 1 | 0 | 1 | 1 | 1 | 0 | 1 | 1 | −1 |
| 1,4-Octadiene | 0 | 0 | 0 | 0 | 0 | 0 | 3 | 1 | 0 |
| 1,3-Octadiene | 0 | 0 | 1 | 0 | 0 | 0 | 3 | 1 | 0 |
| 2-methyl-Pyrimidine | 0 | 0 | 0 | 0 | 0 | 0 | 3 | 1 | 0 |
| 1-Hexanol | 0 | 0 | 0 | 0 | 0 | 0 | 3 | 1 | 0 |
| 2-Heptanone | 0 | 1 | 0 | 1 | 0 | 0 | 3 | 1 | 0 |
| 1,3,5,7-Cyclooctatetraene | 1 | 0 | 0 | 1 | 1 | 1 | 2 | 0 | −1 |
| 2,5-dimethyl-Pyrazine | 0 | 0 | 0 | 0 | 0 | 0 | 3 | 1 | 0 |
| a-pinene | 1 | 1 | 1 | 1 | 1 | 1 | 2 | 0 | −1 |
| Camphene | 0 | 0 | 0 | 0 | 0 | 0 | 3 | 1 | 0 |
| 2-Octanone | 0 | 1 | 0 | 0 | 0 | 0 | 3 | 1 | 0 |
| 1-methyl-4-(1-methylethenyl)-Cyclohexene | 0 | 1 | 0 | 0 | 1 | 0 | 3 | 1 | 0 |
| 2-methyl-Decane | 0 | 0 | 1 | 0 | 0 | 1 | 3 | 1 | 0 |
| Acetophenone | 1 | 1 | 1 | 1 | 0 | 1 | 3 | 1 | 0 |
| 2-Nonen-1-ol | 0 | 0 | 0 | 1 | 0 | 1 | 3 | 1 | 0 |
| 1,10-Dichlorodecane | 0 | 0 | 0 | 0 | 0 | 0 | 3 | 1 | 0 |
| Dodecanal | 0 | 0 | 0 | 0 | 1 | 0 | 3 | 1 | 0 |
| 2-pentyl-Thiophene | 0 | 0 | 0 | 0 | 0 | 0 | 3 | 1 | 0 |
| 2-Decen-1-ol | 0 | 1 | 0 | 1 | 1 | 0 | 3 | 1 | 0 |
| Naphthalene | 1 | 1 | 1 | 1 | 0 | 0 | 3 | 1 | 0 |
| Diethyl Phthalate | 1 | 0 | 1 | 1 | 1 | 0 | 3 | 1 | 0 |
| Index 3I | | | | | | | | | |

| | Incrementation (i) | | | | | | | | |
|---|---|---|---|---|---|---|---|---|---|
| | Weighting (P) | i × P if presence | i × P if absence | Carriage ext | Dwelling 1 | Dwelling 2 | Carriage int | Palace 1 | Palace 2 |
| 1-propanol | 0.08 | 0.08 | 0 | 0.08 | 0 | 0 | 0 | 0.08 | 0.08 |
| Methanecarbothiolic acid | 0.08 | 0.08 | 0 | 0 | 0.08 | 0.08 | 0.08 | 0.08 | 0.08 |
| 3,3-dimethyl-1-Hexene | 0.08 | 0.08 | 0 | 0 | 0 | 0 | 0 | 0 | 0.08 |
| 2-Butanone | 0.08 | 0.08 | 0 | 0.08 | 0.08 | 0 | 0.08 | 0.08 | 0.08 |
| Ethyl Acetate | 1 | 1 | 0 | 1 | 0 | 0 | 0 | 1 | 1 |
| 4-hydroxy-2-Butanone | 0.08 | 0.08 | 0 | 0.08 | 0 | 0 | 0.08 | 0 | 0 |
| 2,2'-Bi-1,3-dioxolane | 1 | 1 | −1 | 1 | −1 | −1 | 1 | 1 | 1 |
| 1-Butanol | 0.08 | 0.08 | 0 | 0.08 | 0 | 0.08 | 0 | 0 | 0.08 |
| 2,5-dimethyl-Furan | 0.08 | 0.08 | 0 | 0 | 0 | 0 | 0 | 0 | 0 |
| 2-ethenyl-2-Butenal | 0.08 | 0.08 | 0 | 0 | 0 | 0 | 0 | 0 | 0 |
| Butyl formate | 0.08 | 0.08 | 0 | 0 | 0 | 0 | 0 | 0 | 0 |
| Pyrazine | 1 | 1 | 0 | 0 | 1 | 1 | 0 | 0 | 0 |
| Pyrrole | 1 | 1 | 0 | 0 | 0 | 1 | 0 | 1 | 0 |
| 1-Pentanol | 0.08 | 0.08 | 0 | 0.08 | 0 | 0 | 0.08 | 0.08 | 0.08 |
| 1-(3,4-dimethylthieno[2,3-b]thiophen-2-yl)-Ethanoneoxime | 1 | 1 | 0 | 0 | 0 | 0 | 1 | 0 | 1 |
| n-Butyl acetate | 0.08 | 0.08 | −0.08 | 0.08 | −0.08 | 0.08 | 0.08 | 0.08 | −0.08 |
| 1,4-Octadiene | 1 | 1 | 0 | 0 | 0 | 0 | 0 | 0 | 0 |
| 1,3-Octadiene | 0.08 | 0.08 | 0 | 0 | 0 | 0.08 | 0 | 0 | 0 |
| 2-methyl-Pyrimidine | 1 | 1 | 0 | 0 | 0 | 0 | 0 | 0 | 0 |
| 1-Hexanol | 0.08 | 0.08 | 0 | 0 | 0 | 0 | 0 | 0 | 0 |
| 2-Heptanone | 0.08 | 0.08 | 0 | 0 | 0.08 | 0 | 0.08 | 0 | 0 |
| 1,3,5,7-Cyclooctatetraene | 0.08 | 0 | −0.08 | 0 | −0.08 | −0.08 | 0 | 0 | 0 |
| 2,5-dimethyl-Pyrazine | 1 | 1 | 0 | 0 | 0 | 0 | 0 | 0 | 0 |

TABLE 4-continued

Emission of VOCs from infested and uninfested environments

| | | | | | | | | | |
|---|---|---|---|---|---|---|---|---|---|
| a-pinene | 0.08 | 0 | −0.08 | 0 | 0 | 0 | 0 | 0 | 0 |
| Camphene | 1 | 1 | 0 | 0 | 0 | 0 | 0 | 0 | 0 |
| 2-Octanone | 0.08 | 0.08 | 0 | 0 | 0.08 | 0 | 0 | 0 | 0 |
| 1-methyl-4-(1-methylethenyl)-Cyclohexene | 0.08 | 0.08 | 0 | 0 | 0.08 | 0 | 0 | 0.08 | 0 |
| 2-methyl-Decane | 1 | 1 | 0 | 0 | 0 | 1 | 0 | 0 | 1 |
| Acetophenone | 0.08 | 0.08 | 0 | 0.08 | 0.08 | 0.08 | 0.08 | 0 | 0.08 |
| 2-Nonen-1-ol | 1 | 1 | 0 | 0 | 0 | 0 | 1 | 0 | 1 |
| 1,10-Dichlorodecane | 0.08 | 0.08 | 0 | 0 | 0 | 0 | 0 | 0 | 0 |
| Dodecanal | 1 | 1 | 0 | 0 | 0 | 0 | 0 | 1 | 0 |
| 2-pentyl-Thiophene | 1 | 1 | 0 | 0 | 0 | 0 | 0 | 0 | 0 |
| 2-Decen-1-ol | 0.08 | 0.08 | 0 | 0 | 0.08 | 0 | 0.08 | 0.08 | 0 |
| Naphthalene | 0.08 | 0.08 | 0 | 0.08 | 0.08 | 0.08 | 0.08 | 0 | 0 |
| Diethyl Phthalate | 0.08 | 0.08 | 0 | 0.08 | 0 | 0.08 | 0.08 | 0.08 | 0 |
| Index 3I | | | | 2.72 | 0.48 | 2.48 | 3.8 | 4.64 | 5.4 |

Calculation of the Value (VL)

The limit value VL was calculated using the formula given in step d-3/ above, namely:

$$VL = \frac{\text{Number of "unweighted } VOCs\text{"} + P \times \text{Number of "weighted } VOCs\text{"}}{\text{Coefficient 2}}$$

It can be seen from Tables 3 and 4 that there are 13 "unweighted VOCs" (since they are only present in the case of infestation) and 23 "weighted VOCs".

In this case, the value VL is equal to 3.71=[13+(0.08×23)]/4.

The values of the index (3I), shown above in Tables 3 and 4, are summarized in Table 5 below.

The uninfested conditions and environments correspond respectively to the first 5 lines of the section "Laboratory conditions" and to the first 3 lines of the section "Environments in situ".

TABLE 5

Values of the indices 3I

| | | Conditions and environments | Value of index 3I |
|---|---|---|---|
| Laboratory conditions | Without infestation | Wool (reference 1) | 2.32 |
| | | Wool (reference 2) | 0.64 |
| | | Previously infested wool 1 | 0.24 |
| | | Previously infested wool 2 | 2.96 |
| | | Rabbit skin (reference) | 1.28 |
| | With infestation | Infested wool 1 | 4.24 |
| | | Infested wool 2 | 7.88 |
| | | Infested wool 3 | 4.80 |
| | | Infested wool 4 | 7.20 |
| | | Infested rabbit skin | 9.28 |
| Environments in situ | Without infestation | Carriage (exterior) | 2.72 |
| | | Dwelling 1 | 0.48 |
| | | Dwelling 2 | 2.48 |
| | With infestation | Carriage (interior) | 3.80 |
| | | Palace 1 | 4.64 |
| | | Palace 2 | 5.40 |

CONCLUSIONS

All of the infested conditions and environments have, as expected, an index (3I) strictly greater than the Limit Value VL (in this case 3.71). In contrast, all of the uninfested conditions and environments have an index less than or equal to this same limit value.

Moreover, the two previously infested conditions have an index below 3.71, reflecting absence of residual VOCs once the infestation is finished and controlled.

The index (3I) therefore correlates well with the activity of the clothes moth, i.e. *Tineola bisselliella*.

The method of the invention for constructing the index (3I) and the value VL therefore advantageously allows detection of insects at the larval stage.

The invention claimed is:

1. A method of detecting the presence of insects in an indoor environment comprising:
    (a) taking a sample of volatile organic compounds (VOCs) in the indoor environment;
    (b) separating the VOCs of the sample;
    (c) detecting the presence or absence of predetermined target VOCs, these predetermined target VOCs belonging to at least one of the following three categories of VOCs:
        VOCs that are emitted independently of a substrate on which the insects grow, and that are only emitted during an insect infestation, called "category 1 VOCs";
        VOCs that are emitted independently of a substrate on which the insects grow but that may also have biological origins other than insects, called "category 2 VOCs"; and
        VOCs that are emitted as a function of a substrate on which the insects grow, and that are only emitted during an insect infestation, called "category 3 VOCs";
    (d) calculating respectively a value for "Insect Infestation Index"(3I) and a value "Limit Value"(VL), each of which depends on the presence or absence of the predetermined target VOCs according to three steps:
        (d-1) determining an incrementing value "i", the incrementing value being obtained by assigning, to each of the predetermined target VOCs, a number −1, 0 or 1 depending on the presence or the absence of the predetermined target VOCS, the numbers being assigned as follows:
        presence of a VOC of category (1) is characterized by the number 1 and the absence by −1;
        presence of a VOC of category (2) is characterized by the number 0 and the absence by −1;
        presence of a VOC of category (3) is characterized by the number 1 and the absence by 0;
        (d-2) determining a weighting value "P" corresponding to the following formula:

$$P = \frac{\text{Coefficient 1}}{\text{Number of weighted } VOCs}$$

in which:
Number of weighted VOCs corresponds to the VOCs found on substrates without active infestation but emitted in a larger relative amount in the presence of the insects, in an amount at least two times higher,
Coefficient 1 is an empirical real number established by iteration with a panel of environments whose infestation is known;
(d-3) determining the value 3I and the value VL, the value 3I corresponding to the following formula:

$$(3I) = \Sigma_{j=1}^{n} i_j \times P_j$$

in which:
n represents the number of target VOCs,
j represents an integer from 1 to n,
i represents the incrementing value as defined in step (d-1), and $i_j$ represents the incrementation of the j-th target VOC,
P represents the weighting value as defined in step (d-2), and $P_j$ represents the weighting of the j-th target VOC,
the value VL corresponding to the following formula:

$$VL = \frac{\text{Number of unweighted } VOCs + P \times \text{Number of weighted } VOCs}{\text{Coefficient 2}}$$

in which:
Number of unweighted VOCs corresponds to the VOCs only emitted in the presence of insects,
P represents the weighting value as defined in step (d-2),
Number of weighted VOCs corresponds to the VOCs found on substrates without active infestation but emitted in a larger relative amount in the presence of the insects, in an amount at least two times higher,
Coefficient 2 is an empirical real number established by iteration with the same environment panel as that used for determining Coefficient 1 as defined in step (d-2); and
(e) comparing the values 3I and the value VL; if the value 3I is strictly greater than the value VL then the environment is infested, and if the value 3I is less than or equal to the value VL, the environment is not infested.

2. The method of detecting the presence of insects as claimed in claim 1, wherein the predetermined target VOCs are selected from the group consisting of 2,2'-bi-1,3-dioxolane; n-butyl acetate; 1,3,5,7-cyclooctatetraene; alpha-pinene; 1-propanol;
methanecarbothiolic acid; 3,3-dimethyl-1-hexene; 2-butanone; ethyl acetate; 4-hydroxy-2-butanone; 1-butanol; 2,5-dimethyl-furan; 2-ethenyl-2-butenal; butyl formate; pyrazine; pyrrole; 1-pentanol; 1-(3,4-dimethylthieno[2,3-b]thiophen-2-yl)-ethanone-oxime; 1,4-octadiene; 1,3-octadiene; 2-methyl-pyrimidine; 1-hexanol; 2-heptanone; 2,5-dimethyl-pyrazine; camphene; 2-octanone; 1-methyl-4-(1-methylethenyl)-cyclohexene; 2-methyldecane; acetophenone; 2-nonen-1-ol; 1,10-dichlorodecane; dodecanal; 2-pentylthiophene; 2-decen-l-ol; naphthalene; diethyl phthalate, and mixtures thereof.

3. The method of detecting the presence of insects as claimed in claim 1, wherein:
the predetermined target category 1 VOCs are selected from the group consisting of 2,2'-bi-1,3-dioxolane and n-butyl acetate;
the predetermined target category 2 VOCs are selected from the group consisting of 1,3,5,7-cyclooctatetraene and alpha-pinene;
the predetermined target category 3 VOCs are selected from the group consisting of 1-propanol; methanecarbothiolic acid; 3,3-dimethyl-1-hexene; 2-butanone; ethyl acetate; 4-hydroxy-2-butanone; 1-butanol; 2,5-dimethyl-furan; 2-ethenyl-2-butenal; butyl formate; pyrazine; pyrrole; 1-pentanol; 1-(3,4-dimethylthieno[2,3-b]thiophen-2-yl)-ethanone-oxime; 1,4-octadiene; 1,3-octadiene; 2-methyl-pyrimidine; 1-hexanol; 2-heptanone; 2,5-dimethyl-pyrazine; camphene; 2-octanone; 1-methyl-4-(1-methylethenyl)-cyclohexene; 2-methyldecane; acetophenone; 2-nonen-1-ol; 1,10-dichlorodecane; dodecanal; 2-pentyl-thiophene; 2-decen-l-ol; naphthalene and diethyl phthalate.

4. The method of detecting the presence of insects as claimed in claim 1, wherein the insects are in the larval state.

5. The method of detecting the presence of insects as claimed in claim 1, wherein:
the insect is *Tineola bisselliella*,
coefficient 1 has a value from 1 to 3, and
coefficient 2 has a value from 3 to 5.

\* \* \* \* \*